United States Patent
Nomaru et al.

(10) Patent No.: US 7,307,233 B2
(45) Date of Patent: Dec. 11, 2007

(54) ISOTOPE SEPARATION METHOD AND WORKING SUBSTANCE FOR ISOTOPE SEPARATION

(75) Inventors: Keiji Nomaru, Kashiwa (JP); Hideki Hattori, Saitama (JP); Yoshiaki Takatani, Kobe (JP)

(73) Assignee: Kawasaki Jukogyo Kabushiki Kaisha, Kobe-shi (JP)

( * ) Notice: Subject to any disclaimer, the term of this patent is extended or adjusted under 35 U.S.C. 154(b) by 0 days.

(21) Appl. No.: 10/548,886

(22) PCT Filed: Dec. 19, 2003

(86) PCT No.: PCT/JP03/16382

§ 371 (c)(1),
(2), (4) Date: Apr. 3, 2006

(87) PCT Pub. No.: WO2005/032697

PCT Pub. Date: Apr. 14, 2005

(65) Prior Publication Data

US 2006/0169574 A1   Aug. 3, 2006

(30) Foreign Application Priority Data

Sep. 30, 2003   (JP) .............................. 2003-341172

(51) Int. Cl.
*C07C 1/00* (2006.01)
*C07F 7/02* (2006.01)
*C07F 7/00* (2006.01)
*C07F 7/12* (2006.01)

(52) U.S. Cl. .................. 204/157.2; 556/400; 556/466; 556/488

(58) Field of Classification Search ............. 204/157.2; 556/400, 466, 488
See application file for complete search history.

(56) References Cited

U.S. PATENT DOCUMENTS 4,824,573 A   4/1989   Honda et al. ............... 210/640

(Continued)

FOREIGN PATENT DOCUMENTS

EP   0 190 758 A1   8/1986

(Continued)

OTHER PUBLICATIONS

Cooper et al., "Polyfluoroalkyl Compounds of Silicon. VIII. Reactions of Silanes with Vinyl Fluoride and with 1-chloro-2-fluoroethylene", J. of the Chem. Soc. (no month, 1967), vol. 12, pp. 2098-2103. Abstract Only.*

(Continued)

*Primary Examiner*—Edna Wong
(74) *Attorney, Agent, or Firm*—Oliff & Berridge, PLC

(57) ABSTRACT

The present invention is directed to the provision of an isotope separation method, which can effectively prevent, without the use of a second gas, a secondary reaction and the formation of a polymer involved in a multiphoton dissociation reaction in laser isotope separation and, at the same time, can efficiently separate a target isotope with low activation energy, and a working substance for use in the isotope separation. The isotope separation method comprises the step of irradiating a working substance for isotope separation comprising a compound represented by formula $SiX_3-CY_2-CZ_3$ or $SiX_3-CY=CZ_2$, wherein X, Y, and Z, which may be the same or different, represent a halogen atom, H, or an alkyl group; and at least one of Z's represents a halogen atom with the remaining Z's being H or an alkyl group, with a laser beam to dissociate only a molecule containing a particular target isotope atom, whereby the dissociation product or the nondissociation molecule is enriched with the target Si isotope atom.

6 Claims, 2 Drawing Sheets

U.S. PATENT DOCUMENTS

| | | | | |
|---|---|---|---|---|
| 6,800,827 | B2* | 10/2004 | Yokoyama et al. | 204/157.2 |
| 2003/0034243 | A1 | 2/2003 | Yokoyama et al. | 204/157.2 |

FOREIGN PATENT DOCUMENTS

| | | |
|---|---|---|
| JP | A 61-181525 | 8/1986 |
| JP | A 62-289224 | 12/1987 |
| JP | A 02-056133 | 2/1990 |
| JP | A 2000-061269 | 2/2000 |
| JP | A 2001-259373 | 9/2001 |
| JP | A 2002-331227 | 11/2002 |
| JP | A 2003-053153 | 2/2003 |

OTHER PUBLICATIONS

Cooper et al., "Polyfluoroalkyl Compounds of Silicon. VIII. Reactions of Silanes with Vinyl Fluoride and with 1-chloro-2-fluoroethylene", J. of the Chem. Soc. (no month, 1967), vol. 12, pp. 2098-2103.*

Liu et al., "Insertion vs. Addition of Oligomeric Difluorosilylenes. Evidence for the Attack of Oligomeric Difluorosilylenes on the Carbon-Carbon Double Bond as an Initial Step in the Insertion Reactions with trans- and cis-Difluoroethylene", J. of the Amer. Chem. Soc., vol. 100, No. 8, Apr. 12, 1978, pp. 2577-2579.*

Sharp et al., "Perfluoro(alkylsilanes). II. Trifluoro(trifluoromethyl)silane and Trifluoro(pentafluoroethyl)silane", Inorg. Chem. (no month, 1972), vol. 11, No. 6, pp. 1259-1264.*

Haszeldine et al., "The Kinetics of the Reactions of Silicon Compounds. Part VIII. The Gas-Phase Thermal Decomposition of Trifluoro-1,1,2,2-Tetrafluoroethylsilane", J. of the Chem. Soc., Perkins Transactions 2: Physical Organic Chemistry (no month, 1972-1999), vol. 7, pp. 1013-1016.*

T. N. Bell et al., "Kinetics of the Thermal Decomposition of β-Trifluoroethylsilanes and Hot Molecule Kinetics of $(CF_3CH_2SiF_3)$", Canadian Journal of Chemistry, 52(18), pp. 3158-3164, 1974, no month.

R. N. Haszeldine et al., "Kinetics of the Reactions of Silicon Compounds. Part VIII. The Gas-phase Thermal Decomposition of Trifluoro-1,1,2,2-Tetrafluoroethylsilane", Journal of the Chemical Society, Perkin Transactions 2: Physical Organic Chemistry, (7), pp. 1013-1017, 1972-1999), no month.

R.N. Haszeldine et al., "The Kinetics of the Reactions of Silicon Compounds. I. The Gas-phase Thermal Decomposition of 2,2-difluoroethyltrifluorosilane", Journal of the Chemical Society, (June), pp. 1890-1894, no year.

K. G. Sharp et al., "Perfluoro(alkylsilanes). II. Trifluoro(trifluoromethyl)silane and Trifluoro(pentafluoroethyl)silane", Inorganic Chemistry, 11(6), pp. 1259-1964, no date.

C. Liu et al., "Insertion vs. Addition of Oligomeric Difluorosilylenes. Evidence for the Attack of Oligomeric Difluorosilylenes on the Carbon-Carbon Double Bond as an Initial Step in the Insertion Reactions with *trans*- and *cis*-difluoroethylene", Journal of the American Chemical Society, 100(8), pp. 2577-2579, no date.

\* cited by examiner

ISOTOPE SEPARATION METHOD AND WORKING SUBSTANCE FOR ISOTOPE SEPARATION

TECHNICAL FIELD

The present invention relates to an isotope separation method, and particularly to an isotope separation method for efficiently separating Si isotopes by laser beam irradiation, and a working substance for the isotope separation.

BACKGROUND OF THE INVENTION

In two molecules, when the type of an isotope constituting one of the molecules is different from the type of an isotope constituting the other molecule, the peak position of a vibration absorption spectrum in the infrared region for one of the molecules is slightly different from the peak position of a visible absorption spectrum in the infrared region for the other molecule. This difference is called "isotope shift." In isotope separation using an infrared laser, molecules including a particular atom as a target for isotope separation are irradiated with a strong infrared laser beam to cause multiphoton dissociation of only the molecule comprising the particular isotope by taking advantage of the isotope shift, whereby the dissociation product or the residual molecule is enriched with the target isotope. Lasers usable herein include carbon dioxide lasers, carbon monoxide lasers, free electron lasers, semiconductor lasers, solid-state lasers, and any other laser which has an oscillation wavelength near 1 to 100 μm.

The abundance ratio of isotopes of natural silicon is $^{28}Si:^{29}Si:^{30}Si=92.23\%:4.67\%:3.10\%$. A technique for laser isotope separation of silicon (Si) is disclosed in Japanese Patent Publication No. 56133/1990. Specifically, this publication proposes a working substance for separating isotopes of Si by laser isotope separation and an isotope separation method using the working substance. This working substance is a fluoromonosilane compound represented by formula $Si_aX_bH_c$ wherein $2 \leq a \leq 3$, $0 \leq b \leq 2a+2$, and $2a+2=b+c$; and X's, which may be the same or different, represent a halogen atom. Japanese Patent Publication No. 13685/1993 proposes, as a working substance for separating isotopes of Si by laser isotope separation, a fluoromonosilane compound represented by $SiFnX_{4-n}$, wherein X represents H, Cl, Br, or I and $1 \leq n \leq 3$, or $SiFnR_{4-n}$ wherein R represents an alkyl group or a halogen derivative thereof and $1 \leq n \leq 3$, and an isotope separation method using the working substance. In this technique, molecules such as $Si_2F_6$ or $SiF_3Br$ are used. Further, $SiF_3H$, $SiF_3Cl$, $SiF_2H_2$, $SiFCl_3$, $SiF_3CH_3$, $SiF_3CF_3$, $SiF_2(CH_3)_2$ and the like are described as examples of target molecules. In particular, $Si_2F_6$ is currently used as a material for studies on practical use of Si isotope separation, because activation energy is low and isotopes can be separated with high efficiency.

In the conventional laser isotope separation methods, however, in many cases, radicals are generated in the course of the reaction. The radicals easily induce a secondary reaction which contributes to lowered selectivity for a target isotope and is causative of the formation of a solid component and a polymer component. The formed polymer component poses serious problems associated with a separation apparatus such as a deterioration in transmittance or damage due to the contamination of the inner surface of the reaction vessel with the polymer or the deposition of the polymer on a laser incidence window. To overcome these problems, for example, a method in which a scavenger gas is mixed to capture the generated radicals and a method in which the formed solid, polymer and the like are regassified by a treating agent for removal and recovery (Japanese Patent Laid-Open No. 259373/2001) have been proposed. The use of the scavenger gas, however, is causative of the dissipation of energy and, further, renders the reaction more complicated. On the other hand, the treatment of the formed solid and polymer more or less disadvantageously causes damage to the laser incidence window.

DISCLOSURE OF THE INVENTION

The present invention is directed to the solution of the above problems of the prior art, and an object of the present invention is to provide an isotope separation method, which can effectively prevent, without the use of a second gas, a secondary reaction and the formation of a polymer involved in a multiphoton dissociation reaction in laser isotope separation and, at the same time, can efficiently separate a target isotope with low energy, and a working substance for use in the isotope separation.

The above object can be attained by an isotope separation method comprising the step of irradiating a working substance for isotope separation comprising a compound represented by formula:

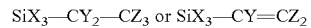
$$SiX_3-CY_2-CZ_3 \text{ or } SiX_3-CY=CZ_2$$

wherein X, Y, and Z, which may be the same or different, represent a halogen atom, H, or an alkyl group; and at least one of Z's represents a halogen atom with the remaining Z's being H or an alkyl group, with a laser beam to dissociate only a molecule containing a particular target isotope atom, whereby the dissociation product or the nondissociation molecule is enriched with the target Si isotope atom.

According to a preferred embodiment of the present invention, in the isotope separation method, Y represents H or an alkyl group.

According to a preferred embodiment of the present invention, in the isotope separation method, the working substance is at least one compound selected from the group consisting of $SiF_3-CH_2-CH_2F$, $SiF_3-CH_2-CHF_2$, $SiF_3-CH_2-CF_3$, and $SiF_3-CH=CHF$.

According to another preferred embodiment of the present invention, in the isotope separation method, the working substance is at least one compound selected from the group consisting of $SiF_3-CHF-CH_2F$, $SiF_3-CHF-CHF_2$, $SiF_3-CHF-CF_3$, $SiF_3-CF=CHF$, $SiF_3-CF_2-CH_2F$, $SiF_3-CF_2-CHF_2$, and $SiF_3-CF_2-CF_2$.

According to a preferred embodiment of the present invention, in the isotope separation method, a multi-wavelength infrared laser is applied simultaneously or after a delay of a given period of time to improve molecular dissociation efficiency and selectivity for isotopes.

The present invention includes an isotope separation method in which a precursor of the working substance which is a compound stable at room temperature is used as a starting material.

Further, according to the present invention, there is provided a working substance for isotope separation, comprising a compound represented by formula:

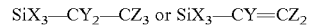
$$SiX_3-CY_2-CZ_3 \text{ or } SiX_3-CY=CZ_2$$

wherein X, Y, and Z, which may be the same or different, represent a halogen atom, H, or an alkyl group; and at least one of Z's represents a halogen atom with the remaining Z's being H or an alkyl group, or a precursor of said compound.

BEST MODE FOR CARRYING OUT THE INVENTION

Figure 1:
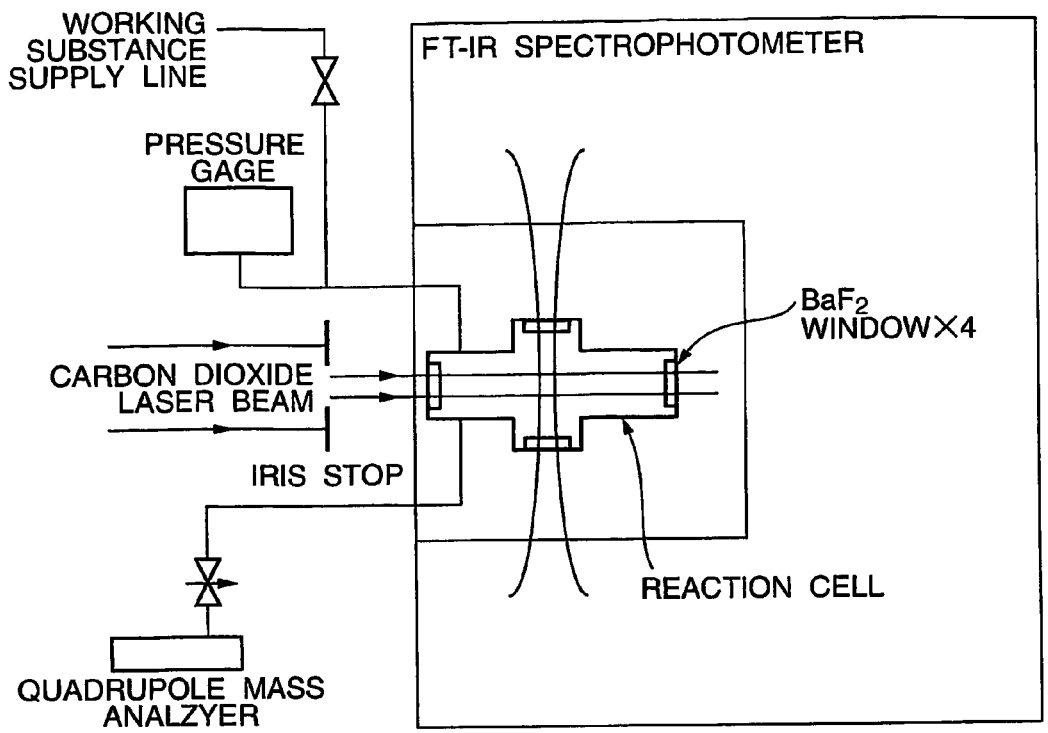
FIG. 1 is a schematic diagram showing an experimental apparatus for isotope separation used in a working example of the present invention which will be described later.

The isotope separation method according to the present invention comprises the step of irradiating a working substance for isotope separation comprising a compound represented by formula $SiX_3$—$CY_2$—$CZ_3$ or $SiX_3$—$CY$=$CZ_2$, wherein X, Y, and Z, which may be the same or different, represent a halogen atom, H, or an alkyl group; and at least one of Z's represents a halogen atom with the remaining Z's being H or an alkyl group, with a laser beam to dissociate only a molecule containing a specific isotope atom, whereby the dissociation product or the nondissociation molecule is enriched with the target Si isotope atom.

The present inventor has aimed at very strong affinity of a halogen for silicon and has made studies on isotope separation of silicon. As a result, the present inventor has found that, when the above specific compound is used as a working substance and is irradiated with a laser beam with a wavelength having selectivity for an isotope, a secondary reaction can be effectively suppressed and, at the same time, isotopes can be separated with low energy. The present invention has been made based on such finding.

What is required for the thermal decomposition of ethylsilane at a relatively low temperature is that at least one dihalogen atom is included in any site of the ethyl group. When the halogen atom is attached to only βC, it has been found that the halogen atom attached to βC is moved to Si through a four-center transition state and only the neutral molecule is provided as a dissociation product without through a radical state.

On the other hand, when the halogen atom is attached to αC, the halogen atom attached to αC is moved to Si through a three-center transition state to form a biradical. This biradical, however, has short lifetime, and, when the concentration of the dissociation product is low, before a reaction with other molecule, the biradical per se is brought to a neutral molecule. Therefore, the generation of this radical has substantially no adverse effect. When the concentration of the dissociation product is high, a secondary reaction is induced. This degree of the secondary reaction, however, is low, and, in both cases, as compared with the conventional technique, the secondary reaction can be significantly reduced.

Regarding these working substances, as in the case of the conventional isotope separation method, the application of a multi-wavelength infrared laser either simultaneous or after a delay of a given period of time can unexpectively improve molecular dissociation efficiency and selectivity for an isotope.

Accordingly, according to a preferred embodiment of the present invention, in the isotope separation method, Y represents H or an alkyl group.

According to a preferred embodiment of the present invention, in the isotope separation method, the working substance is at least one compound selected from the group consisting of $SiF_3$—$CH_2$—$CH_2F$, $SiF_3$—$CH_2$—$CHF_2$, $SiF_3$—$CH_2$—$CF_3$, and $SiF_3$—$CH$=$CHF$.

According to another preferred embodiment of the present invention, in the isotope separation method, the working substance is at least one compound selected from the group consisting of $SiF_3$—$CHF$—$CH_2F$, $SiF_3$—$CHF$—$CHF_2$, $SiF_3$—$CHF$—$CF_3$, $SiF_3$—$CF$=$CHF$, $SiF_3$—$CF_2$—$CH_2F$, $SiF_3$—$CF_2$—$CHF_2$, and $SiF_3$—$CF_2$—$CF_2$.

According to a preferred embodiment of the present invention, in the isotope separation method, as described above, a multi-wavelength infrared laser is applied simultaneously or after a delay of a given period of time to improve molecular dissociation efficiency and selectivity for isotopes.

The present invention includes an isotope separation method in which a precursor of the working substance which is a compound stable at room temperature is used as a starting material. A preferred example of the precursor compound is a compound in which, in the above working substances, the $SiF_3$ portion has been substituted by $SiCl_3$, for example, $SiCl_3$—$CH_2CH_2F$.

EXAMPLE

An experimental apparatus shown in FIG. 1 was used for isotope separation in this example. A working substance is packed into a stainless steel reaction cell having an inner diameter of 40 mm and a length of 190 mm. A $BaF_2$ window having an effective diameter of 14 mm is mounted on both ends of the cell. A carbon dioxide laser beam was applied through this window. The laser beam has a sectional form of 20 mm×20 mm (parallel rays). Just before the cell, the beam was taken off through an iris stop having a diameter of 10 mm and was then introduced into the cell. The laser beam was a pulse laser beam. The pulse width was 100 ns in terms of full width at half maximum, and the laser beam contained a tail pulse having a low intensity of about 2 μs.

Figure 2:
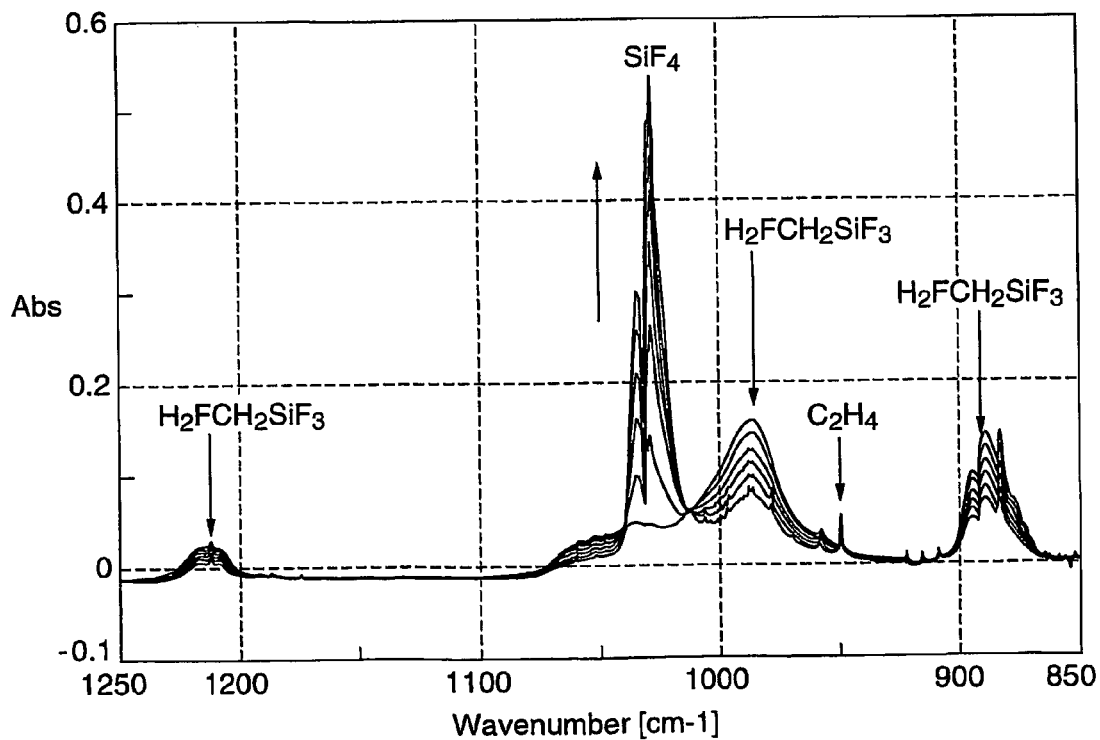
FIG. 2 is a graph showing a change in an infrared absorption spectrum in a working example which will be described later.

The working substance used was 2-fluoromethyltrifluorosilane ($H_2FC$—$CH_2$—$SiF_3$). The packing pressure of the working substance during the experiment was 0.1 Torr. The working substance was irradiated with the carbon dioxide laser of which the irradiation wavelength was tuned to 10R26 (980 cm$^{-1}$). As a result, it was found that the working substance was decomposed at a very low irradiation intensity of 100 mJ/cm$^2$. An FT-IR spectrum shown in FIG. 2 obtained by carbon dioxide laser irradiation reveals that the reaction path can be expressed by formula (1). In this connection, it should be noted that absorption spectra for $SiF_4$ and $C_2H_4$ are known.

$$H_2FC\text{—}CH_2\text{—}SiF_3 + nh\nu \rightarrow SiF_4 + C_2H_4 \qquad (1)$$

Figure 3:
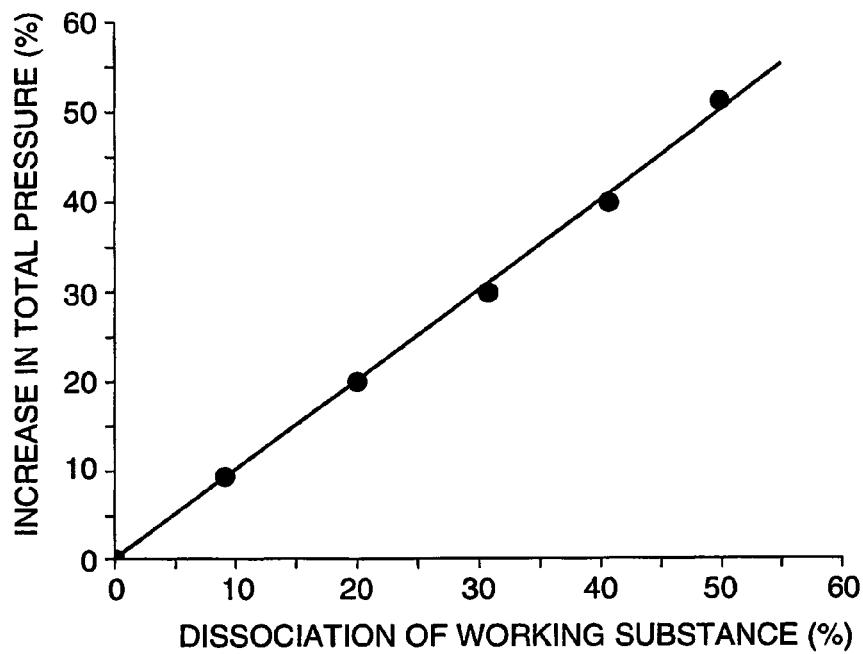
FIG. 3 is a graph showing a relationship between the dissociation of a working substance and an increase in total pressure upon carbon dioxide laser irradiation in a working example which will be described later.
Figure 4:
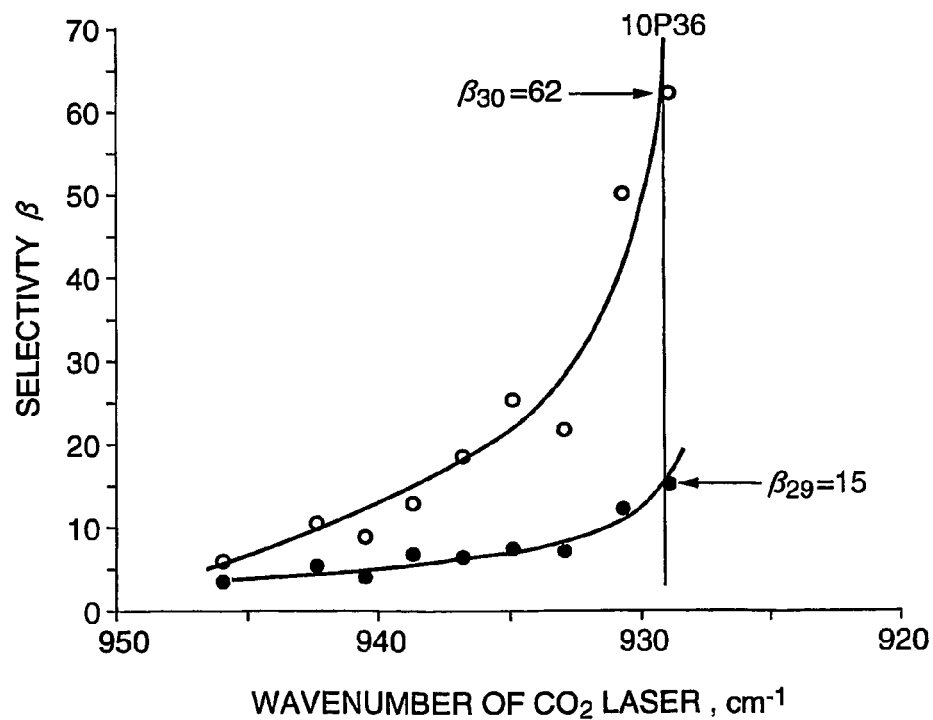
FIG. 4 is a graph showing the wavelength dependency of selectivity for an isotope in a working example which will be described later.

Here nhv represents photon energy of a carbon dioxide laser absorbed in the molecule. Further, as shown in FIG. 3, the increase (%) in pressure involved in the reaction is proportional to the dissociation (%) of the working substance, and, even after a plurality of experiments, neither the deposition of any material on the reaction cell window nor the contamination of the inside of the cell was observed. These facts demonstrate that, in the present process, any secondary reaction other than the reaction expressed by formula (1) does not occur. The wavelength dependency of selectivity for isotopes (defined as $\beta_{29}=k_{29}/k_{28}$, $\beta_{30}=k_{30}/k_{28}$; ki (i=28, 29, 30) is the dissociation rate constant of each isotope) given by the ratio of dissociation rate constants of individual isotope-containing molecules (defined as the dissociation (%) of each isotope-containing molecule per laser pulse irradiation) was measured. The results (irradiation energy density of carbon dioxide laser: 350 mJ/cm²) are shown in FIG. 4. When the irradiation wavelength of the $CO_2$ laser was 10P36 (929 cm$^{-1}$), the residual working substance was enriched with $^{28}$Si in a proportion of 98% at 500 shots and substantially 100% at 2000 shots. The selectivity for isotopes was $\beta_{29}$=15 and $\beta_{30}$=62.

The invention claimed is:

1. An isotope separation method comprising the step of irradiating a working substance for isotope separation comprising a compound represented by formula:

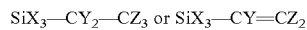

wherein each independent X, Y, and Z, which may be the same or different, represent a halogen atom, H, or an alkyl group; and at least one of the Z's represents a halogen atom with the remaining Z's being H or an alkyl group, with a laser beam to dissociate only a molecule containing a particular target isotope atom, thereby condensing the target isotope atom in a dissociation product or a nondissociation molecule.

2. The isotope separation method according to claim 1, wherein Y represents H or an alkyl group.

3. The isotope separation method according to claim 2, wherein the compound is at least one compound selected from the group consisting of $SiF_3$—$CH_2$—$CH_2F$, $SiF_3$—$CH_2$—$CHF_2$, $SiF_3$—$CH_2$—$CF_3$, and $SiF_3$—$CH$=$CHF$.

4. The isotope separation method according to claim 1, wherein the compound is selected from the group consisting of $SiF_3$—$CH_2$—$CH_2F$, $SiF_3$—$CH_2$—$CHF_2$, $SiF_3$—$CH_2$—$CF_3$, and $SiF_3$—$CH$=$CHF$.

5. The isotope separation method according to claim 1, wherein the compound is selected from the group consisting of $SiF_3$—$CHF$—$CH_2F$, $SiF_3$—$CHF$—$CHF_2$, $SiF_3$—$CHF$—$CF_3$, $SiF_3$—$CF$=$CHF$, $SiF_3$—$CF_2$—$CH_2F$, $SiF_3$—$CF_2$—$CHF_2$, and $SiF_3$—$CF_2$—$CF_3$.

6. The isotope separation method according to claim 1, wherein the laser beam is a multi-wavelength infrared laser beam and the laser beam is applied simultaneously or after a delay of a given period of time to improve molecular dissociation efficiency and selectivity for isotopes.

* * * * *